United States Patent [19]
Snell et al.

[11] Patent Number: 6,108,579
[45] Date of Patent: Aug. 22, 2000

[54] BATTERY MONITORING APPARATUS AND METHOD FOR PROGRAMMERS OF CARDIAC STIMULATING DEVICES

[75] Inventors: Jeffrey D. Snell, Oak Park; J. Kelly Fox, Valencia, both of Calif.

[73] Assignee: Pacesetter, Inc., Sylmar, Calif.

[21] Appl. No.: 08/832,717

[22] Filed: Apr. 11, 1997

Related U.S. Application Data

[60] Provisional application No. 60/015,972, Apr. 15, 1996.

[51] Int. Cl.[7] .............................. A61N 1/37; A61N 1/372; H01M 10/48
[52] U.S. Cl. ................................. 607/29; 429/90; 429/92
[58] Field of Search ......................... 429/90, 92; 607/29, 607/27

[56] References Cited

U.S. PATENT DOCUMENTS

| | | | |
|---|---|---|---|
| 4,556,061 | 12/1985 | Barreras | 128/419 PT |
| 5,391,193 | 2/1995 | Thompson | 607/29 |
| 5,458,624 | 10/1995 | Renirie et al. | 607/29 |
| 5,620,474 | 4/1997 | Koopman | 607/29 |

OTHER PUBLICATIONS

Gerrard, Douglas J., "Pacemaker Longevity Modelling," *Pace*, vol. 11, pp. 302–307 (Mar. 1988).

*Primary Examiner*—Carol Chaney

[57] ABSTRACT

A system and method for predicting and displaying a realistic time remaining to a recommended replacement time (RRT) of a battery of a implantable cardiac stimulating device or similar battery powered medical device is provided.

39 Claims, 5 Drawing Sheets

BATTERY MONITORING APPARATUS AND METHOD FOR PROGRAMMERS OF CARDIAC STIMULATING DEVICES

This application claims the benefit of U.S. Provisional Application No. 60/015,972, filed Apr. 15, 1996.

FIELD OF THE INVENTION

The present invention relates to a system and method that allow a physician to determine the time remaining to the recommended replacement time of a battery supplying power to an implantable cardiac stimulating device.

BACKGROUND OF THE INVENTION

The typical adult sinus rhythm range is between 65 and 85 heart beats per minute (bpm). Generally, rates between 60 and 100 bpm are not a cause for concern. This range is called the sinus rate range. Rates falling outside the sinus rate range are known as arrhythmias. An arrhythmia in which the sinus rate is above 100 bpm is called tachycardia. An arrhythmia in which the sinus rate is below 60 bpm is called bradycardia.

Pacing devices are used to provide artificial cardiac pacing to patients exhibiting bradycardia. It is increasingly more common to combine pacing devices with cardioverter/defibrillator devices. This allows a physician to prescribe a single cardiac stimulating device that is capable of administering treatment for bradycardia, tachycardia and fibrillation.

Because these devices are implanted into a patient's body, they necessarily are powered by an internal energy source. The lack of a suitable energy source was a major impediment to the development of modern implantable cardiac devices. Initially, mercury zinc cells were used, but were unable to provide the peak current requirements of cardioverters which typically are in the range of one to two amperes for approximately 10 seconds. Lithium vanadium pentoxide batteries were able to meet this requirement, but had a characteristic precipitous voltage decline towards the end of their usable life. These batteries were abandoned because of the difficulty in accurately determining the remaining life of the battery.

Currently, lithium silver vanadium pentoxide cells are favored for powering high voltage circuitry in cardioverter/defibrillators and lithium iodine cells are favored for powering low voltage circuitry. These batteries are favored for two reasons: (1) they have greater energy density than their predecessors, more charge stored per unit of battery volume combined with a lower internal impedance; and (2) they have a gradual voltage decline over their usable life. The latter characteristic allows a more accurate prediction of when the battery's usable life is near its end.

The newer Lithium/Carbon Monoflouride (Li/CFx) cells, manufactured by Wilson Greatbach, LTD, Clarence, N.Y., provide a medium current capability with a very low internal impedance characteristic.

Because time and usage both degrade the abilities of all batteries to supply power, physicians need to be able to predict when surgical replacement of the battery (or the entire device) will be needed. For patients who are dependent on the device, timely replacement of the battery is critical. For that reason, the physician needs accurate data on remaining battery life in order to properly schedule replacement surgery.

Present systems do not adequately enable physicians to forecast the time when replacement surgery should be scheduled. Present systems, known in the art, typically base the recommended replacement time (RRT) on the assumption that the device could operate at (worst case) 100% pacing at the current programmed settings and at the current current drain. Prior systems do not take into consideration such factors as elevated/lowered rates due to activity, metabolic demand circadian rhythms (sleep modes), P-wave tracking and/or R-wave inhibition, or lowered current drain modes due to automatic features (e.g., autocapture).

Nor do the prior known systems take into account the reduction in current drain which varies according to the declining battery voltage as a result of the ohmic circuits and the starvation of the charge pump circuitry (which results in voltage/current limited stimulation pulses). It is well known that a battery's internal impedance increases with time and usage. As a battery's internal impedance increases, the terminal voltage of the battery decreases because more voltage is lost across the battery's internal impedance which tends to act like a voltage divider circuit. The decrease in terminal voltage eventually reaches a point where the battery cannot supply the voltage needed to operate an implantable cardiac stimulating device. That voltage corresponds to the battery's end of life. Typically, batteries have a recommended replacement time ("RRT") which corresponds to a voltage slightly higher than the battery's end of life voltage. The difference between the two creates a margin of error.

The discharge characteristics of batteries can be expressed by curves (or equations) of internal battery impedance as a function of expended battery capacity (in terms of charge). Internal battery impedance can be measured directly or may be derived by, for example, measuring the terminal voltage of the battery and the load resistance and applying Ohm's law to find a normalized current flow as expressed in the equation $$I = V/R_t = V_{oc}/(R_L + R_b)$$

where V is the measured battery voltage, $R_t$ is total resistance, $R_b$ is internal battery impedance, $V_{oc}$ is the battery open circuit voltage, I is normalized current, and $R_L$ is the load resistance. It follows that:

$$R_b = (\Delta V/V) R_L;$$

where $\Delta V = V_{oc} - V$.

The relationship between charge depleted (Q) and internal battery impedance may be depicted in a look-up table format or a graphical format which represents corresponding values of $R_b$ and Q for each resistive load. By using variations of the equation T=Q/I where T is time, Q is charge, and I is the battery current drain, the time it takes to deplete a selected amount of battery charge may be determined.

Previously known programming devices use variations of the foregoing expressions to display some indication of the recommended replacement time of a battery. For example, previously known devices may, upon interrogation of an implanted device, display that the recommended replacement time has been reached, or may display the percent of battery depletion. Previously known devices do not allow a patient or a physician to easily and accurately determine the time remaining to the recommended replacement time.

What is needed therefore is an automatic and amenable system and method of forecasting and displaying the time remaining to the recommended replacement time of the battery. Furthermore, the system and method should be able to be practiced with existing implantable pacemakers, cardioverters, defibrillators or any combination thereof.

SUMMARY OF THE INVENTION

The disadvantages and limitations of previously known devices are overcome by the present invention. With this invention, a system and method for accurately forecasting a time remaining to a battery's recommended replacement time ("RRT") are provided without the need for additional hardware. In addition, the system is capable of predicting and displaying the time remaining to the recommended replacement time.

It has been realized that because replacement of an implanted cardiac stimulating device's battery typically involves a surgical procedure, patients, as well as physicians, need to know when to expect to undergo such surgery. The present invention overcomes the shortcomings of previously known devices by allowing a patient to plan the time that he or she will undergo the replacement surgery without the need for abruptly scheduling a device replacement procedure following the onset of an RRT indicator.

The system of the present invention includes an implantable cardiac stimulating device for administering a therapeutic charge to a heart through a lead system. The lead system also serves to sense intrinsic cardiac activity during periods when therapy is not being applied. In doing so, the lead system receives analog signals from the heart that represent intrinsic cardiac activity and transmits them to a sensing circuit. The sensing circuit amplifies and digitizes the analog signals to produce signals that are readable by a processor. The pacemaker processor analyzes the received digital signals to determine whether or not an arrhythmia exists. The pacemaker processor performs this analysis by employing routines stored in memory. When the pacemaker processor detects the existence of an arrhythmia, a pulse generation and delivery circuit is enabled and proceeds to generate the appropriate therapeutic charge to convert the arrhythmia occurring. The pulse generation and delivery circuit is powered by a battery.

As the battery is the only energy source available to the pacemaker, it is important that its operation be monitored to facilitate assessments of whether it is operating properly and how long it will continue to do so. A monitoring circuit monitors various battery parameters which are indicative of the battery's performance. These battery parameters include battery voltage, the current drain on the battery, and preferably internal battery impedance. The monitoring circuit may also monitor device operational parameters such as the programmed amplitude, waveform, and the rate of therapy. All parametric data are stored in a memory.

The current consumption of pacemakers and ICDs differ as follows. A bradycardia pacing device consumes current for each of: relatively low voltage cardiac pacing pulses and also for the quiescent (i.e., maintenance) current of so-called "ohmic circuits" (i.e., digital circuits). Whereas a typical ICD which, with a bradycardia pacing capability, consumes current for very low voltage ATP pulses (i.e., antitachycardia pacing), low voltage cardioversion pulses, and high voltage defibrillation shocks.

A telemetry circuit accesses the stored parametric data and transmits it to an external programmer. A telemetry head on the programmer receives the parametric data from the telemetry circuitry of the implantable cardiac stimulating device and conveys that data to a telemetry interpreter of the programmer. The telemetry interpreter decodes the received data and transmits the decoded data to a raw telemetry memory that is used to buffer the decoded data. The data in the telemetry memory is decoded by the controller which analyzes the decoded data in a predetermined manner to compute a forecasted time remaining to the RRT.

In order to compute the time remaining to the RRT, the present invention needs to know the charge available for implantable device operation during the interval between the time of interrogation and the RRT. It also needs to know the rate at which that remaining available charge will be depleted, i.e., a predicted current drain. The remaining battery capacity at the RRT depends on the specific instantaneous current at the RRT. Since RRT is identified as the operational point at which the battery internal voltage drop has caused the battery terminal voltage to fall below a predetermined RRT voltage, the current near RRT determines whether RRT has been reached.

The difference between the charge depleted up to the RRT and the charge depleted up to the time of interrogation represents the charge remaining to the RRT. Once the charge remaining to the RRT is known, the time remaining to the RRT may be determined.

The prediction of time remaining to the RRT is then sent to a storage memory to be stored until a display of that data is requested. When requested, the storage memory sends the data to a display logic circuitry which formats the data for display. The display logic circuitry then sends the formatted data to a display terminal for viewing. The manner of display, for example text or graphical, is a matter of design choice, but in accordance with the present invention the display should give the physician at least the forecasted time remaining to the recommended replacement time, as for example, "Time Remaining to RRT: 17 months."

As stated, the time remaining to the RRT is determined by first calculating the battery charge depleted up to the RRT. To calculate the battery charge depleted at any given time, the controller accesses a memory containing the battery discharge relationships which allow the controller to convert the measured battery voltage and measured battery current to the corresponding internal battery impedance which is in turn converted to a corresponding battery charge depleted.

When calculating the battery charge depleted up to the RRT, a preselected voltage corresponding to the RRT is used in the above calculations. When calculating the battery charge depleted at the time of interrogation, the measured battery voltage at that time is used. Alternatively, if the implantable cardiac stimulating device is capable of monitoring its internal battery impedance, the battery impedance at the time of the interrogation may be telemetered to the programmer which then determines the battery charge depleted as a function of the battery impedance. In pacemakers that do not have the capability to measure battery impedance directly, battery impedance at time of interrogation also may be calculated by measuring the battery voltage and battery current and calculating $R_I=(V_{oc}-V_{meas})/I_{meas}$.

An approach, which is known in the art, is to interrogate the pacemaker to obtain the current available battery charge and subtract this charge from the battery charge which will cause the pacemaker to go into the RRT mode. By dividing the result by the normalized current drain on the battery, the time remaining to the RRT is determined and may be displayed to the physician.

As an improvement over the prior art, a preferred embodiment of the present invention more closely predicts the future battery current drain from the time of interrogation until the estimated RRT. The battery charge depleted up to interrogation is determined just as described above. However, instead of dividing the usable charge by the normalized current to get the time remaining to the RRT, the preferred embodiment employs a computer simulation of the operation of the implantable device to more accurately predict the current drain on the battery.

The computer simulation closely predicts the operation of the implantable cardiac device for a simulated pre-set time period or episode. At the end of the episode, the computer calculates the charge depleted during that simulated time period. That value is added to the charge depleted up to interrogation. For example, a two second computer simulation episode may simulate an operational period of two months and deplete 10 coulombs (C) of battery charge during that simulated period. The computer simulation further includes simulations of the effects of the declining battery voltage and current drain on the ohmic circuits and charge pump circuitry.

In the case of simulating the operation of an ICD, in addition to simulating the bradycardia pacing pulses, the sporadic cardioversion shocks must also be simulated. Although the individual cardioversion shocks are high energy, the overall current consumption of the bradycardia pacing and the intrinsic current consumed by the ohmic circuits predominates.

As time passes, due to the normal decline of the battery voltage, current drain declines because of the effects of charge pump starvation and the resistive circuits. The computer simulation of the present approach advantageously accounts for the effects of delivered therapy and time on the battery current drain to more accurately predict the time remaining to the RRT.

To determine the battery current drain more accurately the programmer accounts for charge pump starvation, for the ohmic resistance of the implantable device along with the battery's internal impedance, the therapeutic pulse width, the therapeutic pulse amplitude, the lead impedance(s) and the programmed rate of stimulation delivery. These parameters are retrieved from the implantable cardiac device at interrogation. Each subsequent calculation of the current drain includes the simulated effect of each delivered therapy on each parameter. The current drain on the battery is recalculated after each episode.

As stated, after each episode the charge depleted during that episode is calculated and added to the actual battery charge depleted at the time of interrogation. That cumulative depleted charge is used to determine the new battery impedance which in turn is used to calculate the new battery voltage. These newly calculated battery voltages are used to identify when RRT has been reached. At that point, the time frames represented by each simulated episode can be added together, or the number of simulated episodes can be counted and the time frame of one episode can be multiplied by the number of episodes to obtain the forecasted time remaining to the RRT.

It is desirable that the simulated time frame of each episode be as short as practically possible in order to maximize the accuracy of the time remaining time to the RRT prediction. Because the present embodiment employs a computer simulation of stimulation episodes, a more powerful controller is needed to enable calculation of the time remaining to the RRT within a practical time period.

In another embodiment of the invention, the implantable cardiac stimulating device has the ability to calculate the charge depleted by each administered therapeutic pulse or the charge depleted during a selected time frame. The device then keeps a cumulative record of those results. When determining the battery charge depleted at interrogation, the programmer of the present invention simply retrieves the cumulative record from the implantable cardiac stimulating device upon interrogation. Either the prior art embodiment or the preferred embodiment of the present invention may be employed thereafter to determine the time remaining to the RRT. This embodiment of the present invention has the advantage of providing the most accurate prediction of the RRT since the actual charge depleted at interrogation, as tracked by the implantable cardiac stimulating device, is used in forecasting the RRT rather than converting the internal battery impedance to a corresponding charge depleted value.

In yet another embodiment of the present invention, the programmer advantageously uses event data to provide an even more accurate prediction of the time remaining to the RRT by accounting for the impact of a variety of lifestyles on the battery charge depleted. For example, if a very active person has a rate responsive pacemaker implanted, that person will demand a premium in terms of the charge required to sustain his lifestyle as opposed to a sedentary person.

Battery longevity forecasting is enhanced by using long term "event data" collected by certain classes of pacemakers. From this data, the programmer extracts the percent pacing in each of the ventricular and atrial chambers and an average pacing rate.

The use of such event data (from Event Histograms) assumes that this historical event data is representative of future heart-pacemaker performance. The basic version of Algorithm #1 (Direct Calculation), $t = Q_{remain}/I_{meas}$ and Algorithm #3 (Pacemaker Charge Counting) assumes 100% pacing at the programmed rate. For many implantations, this simplification may lead to a pessimistic forecast because there is no allowance for current savings gained due to pacemaker inhibition by the native heart activity in some cycles. Nor are the effects of P-wave tracking by the pacemaker in the ventricular channel and effects of rate modulated pacing on the pacing rate addressed by the basic algorithms. Ignoring such current consuming rate elevations may lead to an overly optimistic forecast.

It is preferable that $I_{meas}$ should be weighted by the % pacing and the pacing rate average. For example in a single-chamber pacemaker, the future current consumption (between the time of interrogation and RRT) is best approximated by weighting the measured current according to data obtained from such event data as follows:

$$I_{predicted} = \% \text{ Pacing} * I_{meas} * (RATE_{avg}/RATE_{programmed})$$

The basic version of preferred embodiment (Simulation) t=SUM (pacing episodes) also assumes 100% pacing at the programmed rate. This embodiment is also enhanced by scaling the number of pulses in each episode by the "% pacing" and the "average pacing rate" from the event data. In a dual-chamber implantation, forecasting is further enhanced by appropriately applying the differential pacing % in each chamber. The Pulse Amplitude and Pulse Width are individually programmable for each chamber in typical pacemakers and the lead impedances of the two channels could be dissimilar. So it can be seen that individually scaling the total number of pulses in each channel is advantageous.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DESCRIPTION OF THE PREFERRED EMBODIMENTS

Figure 1:
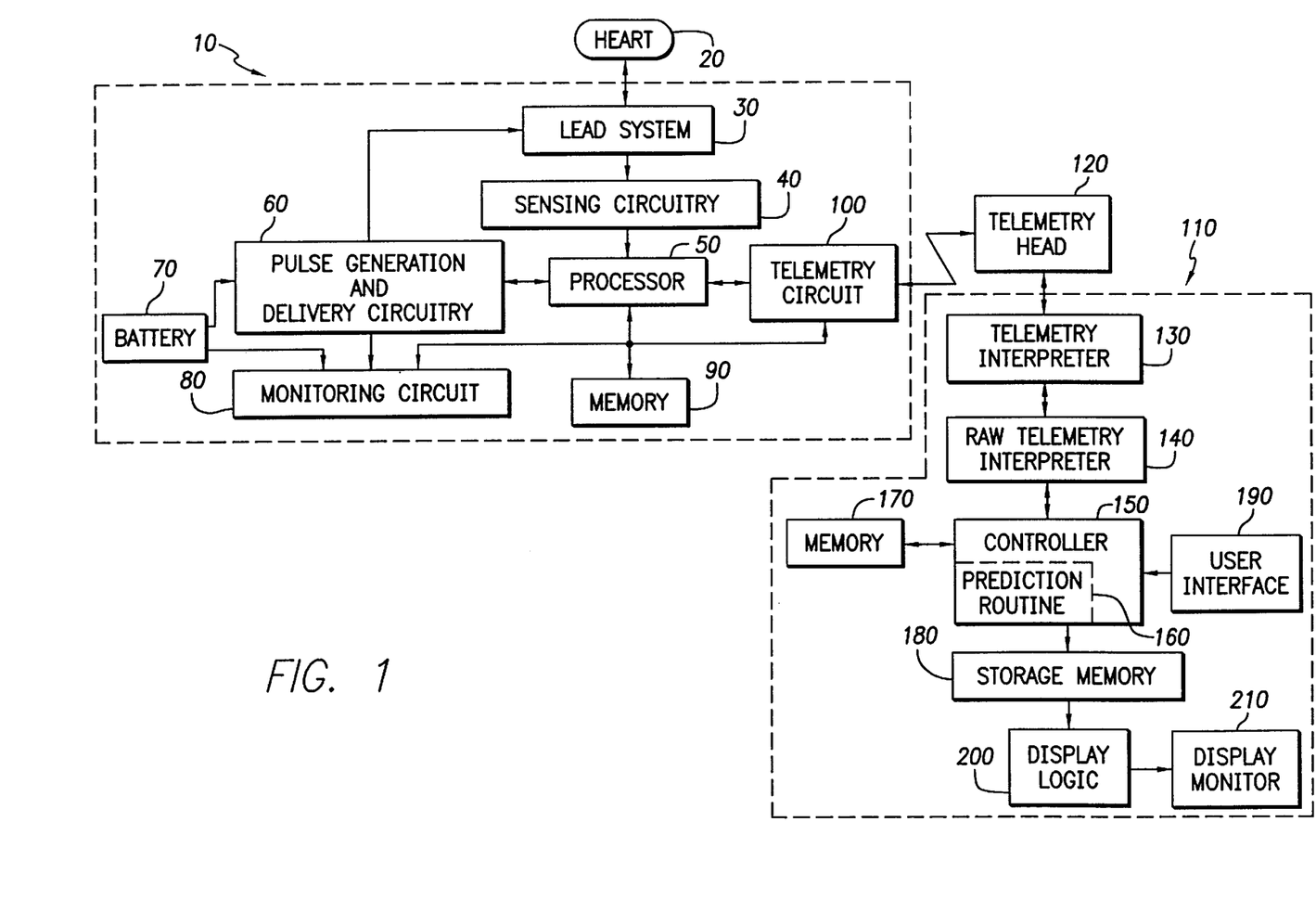
FIG. 1 is a block diagram of a system for forecasting and displaying the time remaining to a recommended battery replacement time which includes a implantable cardiac stimulating device and an associated programmer.

In FIG. 1, a system for determining the time remaining to a battery's recommended replacement time is described. The system includes an implantable cardiac stimulating device 10 for providing electrical stimulation to a patient's heart 20. The electrical stimulation is applied to the heart 20 through a lead system 30. The lead system 30 also senses intrinsic cardiac activity in the form of analog electrical signals (not shown). Those signals are transmitted to a sensing circuit 40 that amplifies and digitizes the received analog signals for use by a processor 50.

The processor 50 performs all of the logic operations required to analyze the digitized signals to detect the occurrence of an arrhythmia, classify the type of arrhythmia occurring, and to administer the appropriate therapy. After an arrhythmia is detected and classified, the processor 50 informs a pulse generation and delivery circuit 60 to begin generating a charge of sufficient energy to effectuate the therapy prescribed by the processor 50.

A monitoring circuit 80, as described in commonly assigned U.S. Pat. No. 5,507,786, issued Apr. 16, 1996, of Mann and Morgan entitled "System and Method for Measuring and Storing Parametric Data Pertaining to Operating Characteristics of an Implantable Medical Device", which is hereby incorporated by reference, monitors the operation of the device 10 and the battery 70. The monitoring circuit 80 stores in a memory 90 data indicative of the battery's 70 performance including its output voltage, current drain, and preferably its internal impedance, charge depleted to date, pulse amplitude and width, rate and lead impedance.

The implantable cardiac stimulating device 10 includes a telemetry circuit 100 which enables communication with a programmer 110 through a telemetry head 120. The telemetry circuit 100 is capable of communicating to the programmer 110 data stored in the monitoring circuit 80, the processor 50, or the memory 90.

The telemetry head 120 receives and conveys the data to a telemetry interpreter 130. The telemetry interpreter 130 decodes the received data and transmits the decoded data to a raw telemetry memory 140 which is used to buffer the decoded data. The raw telemetry memory 140 transmits the decoded data to a controller 150 that contains a prediction routine 160 for analyzing the decoded data in a predetermined manner to compute a forecasted time remaining to the battery's recommended replacement time.

In computing the time remaining to the RRT, the controller 150 accesses a memory 170 containing battery discharge relationships from which the battery charge depleted as a function of battery impedance may be determined. The controller 150 determines the difference between the battery charge that will be depleted at the RRT and the battery charge depleted at interrogation. The controller 150 then computes the time remaining to the RRT by dividing that result by the current drain on the battery 70 and transmits its prediction to a storage memory 180 to be stored until a display of that result is requested by a user of the programmer 110. User requests and data inputs to the programmer are made by way of a user interface 190. When requested by a user, the storage memory 180 sends its stored data to a display logic circuit 200 which formats the data into a displayable form. The display logic circuit 200 then sends the formatted data to a display monitor 210 for viewing. The manner of displaying the time remaining to the RRT, for example textual or graphical, is a matter of design choice, but in accordance with the present invention the display should give the physician at least the time remaining to the RRT, as for example "Estimated replacement time: 17 months".

Figure 2:
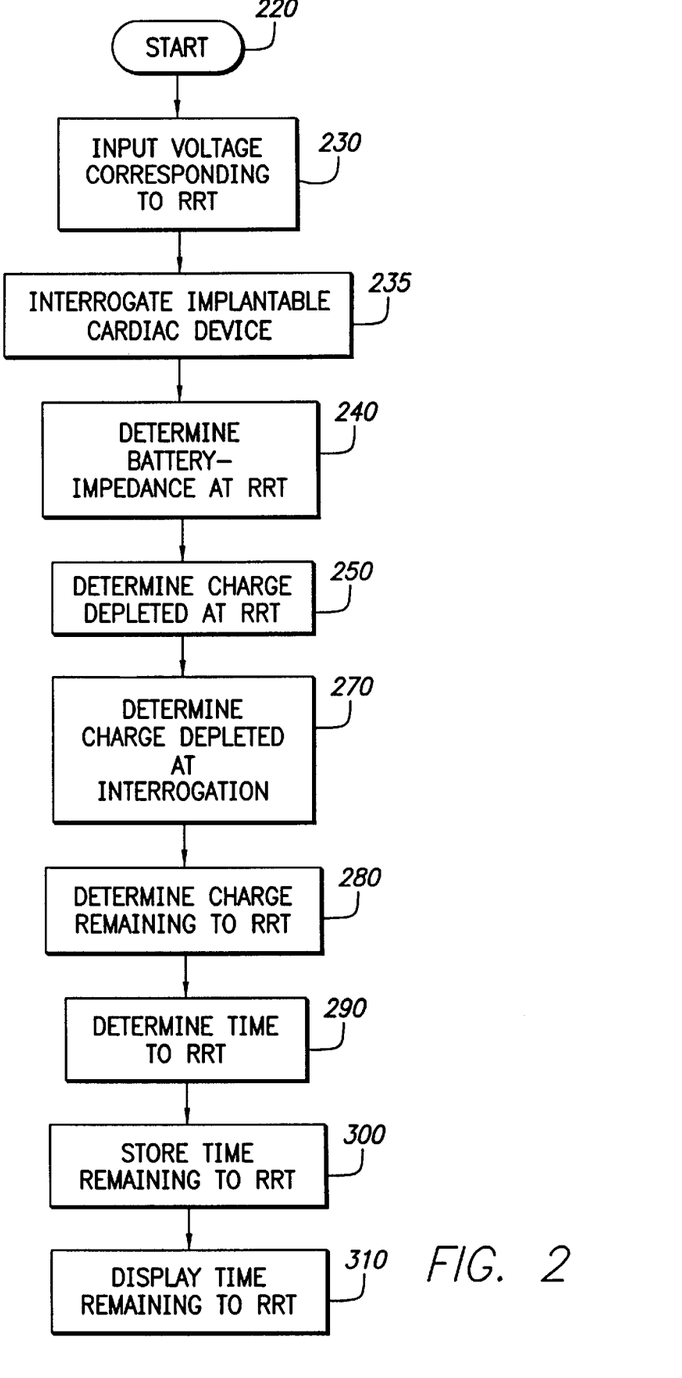
FIG. 2 is a logic flow diagram of a routine run by the controller of FIG. 1 for determining to a first approximation the time remaining to a battery's recommended replacement time, as is known in the prior art.

In FIG. 2, a logic flow diagram representing a program executed by the controller 150 for determining the time remaining to the RRT via a "direct calculation" method is described, as is known in the prior art. After a start 220, at a step 230, a user inputs into the controller 150 a voltage corresponding to the battery voltage at the RRT by way of the user interface 190.

As shown in FIG. 2 at a step 235, the implanted cardiac stimulating device 10 is interrogated by the programmer 110 to retrieve programmed parameters, measured lead impedance, and battery data. Some existing implantable cardiac stimulating devices may be capable of monitoring internal battery impedance, and for those devices, that data is also retrieved at step 235.

At a step 240, the controller 150 determines the internal battery impedance which occurs at the RRT based on the predetermined battery voltage at the RRT and estimated battery current at the RRT by employing the relationships stored in memory 170. At a step 250 the controller 150 determines the charge delivered by the battery at the RRT by employing the battery impedance determined at step 240 and the relationships stored in memory 170.

Figure 3:
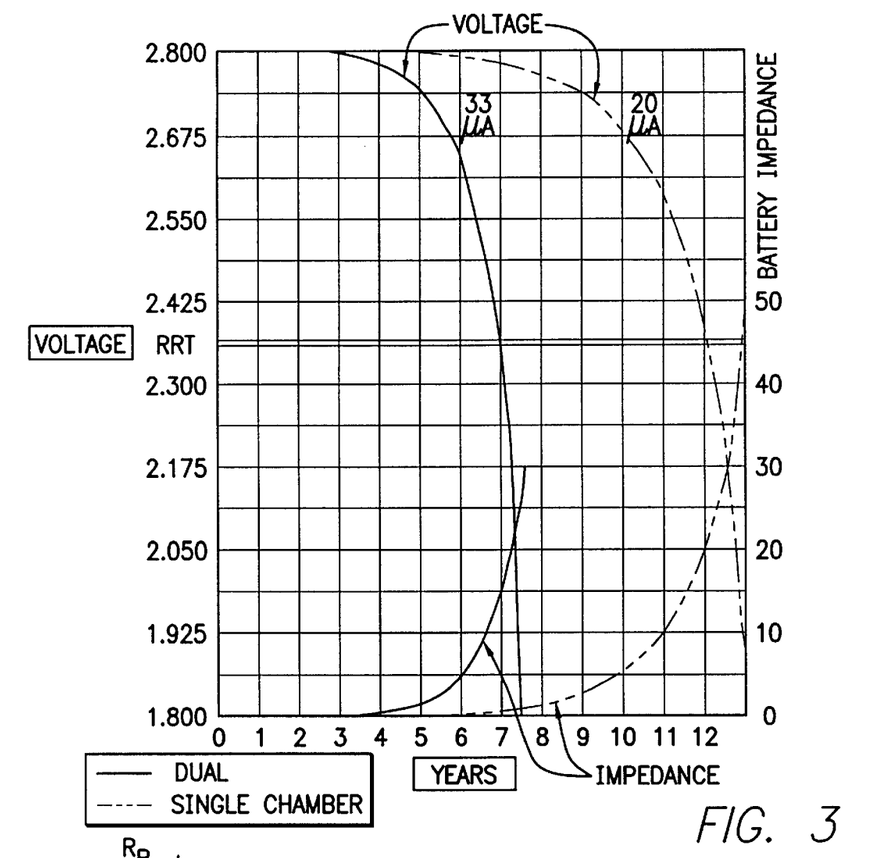
FIG. 3 is a plot of battery voltage and impedance as a function of time for the given battery current drains for a typical pacemaker.

In FIG. 3, a graphical representation of the relationship between battery voltage and impedance as a function of time is shown.

Figure 4:
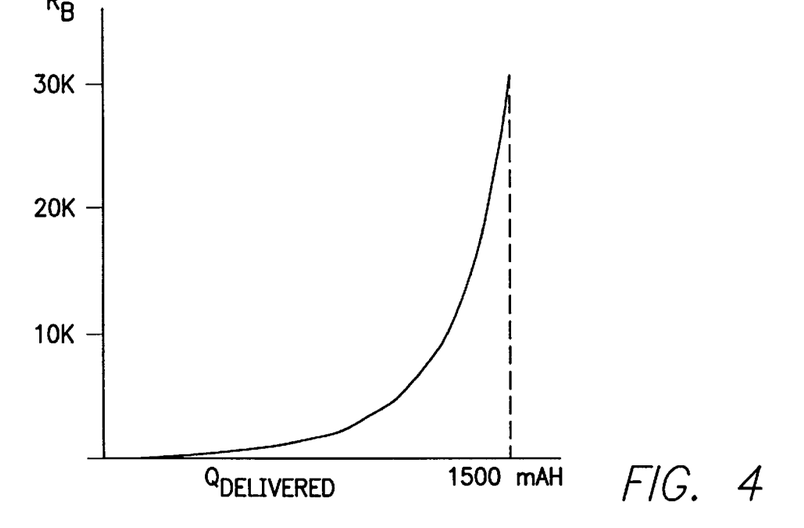
FIG. 4 is a plot of internal battery impedance as a function of charge delivered for a typical lithium/iodine battery.

In FIG. 4, a graphical representation of the relationship between battery-impedance and charge delivered is shown. The relationship of FIG. 4 may be stored in memory 170 in either a look-up table format (not shown) or as an equation.

At a step 270, in FIG. 2, the controller 150 determines the battery charge depleted at the time of interrogation by employing the battery impedance interrogated in step 235 and the battery relationships stored in memory 170. At a step 280 the controller 150 subtracts the battery charge depleted at interrogation from the battery charge that will be depleted at the RRT to obtain the charge remaining to the RRT. At a step 290, the controller 150 divides the charge remaining to the RRT by the telemetered battery current drain to obtain the time remaining to the RRT. At a step 300, the controller 150 transmits the time remaining to the RRT to the storage memory 180. At a step 310 the time remaining to the RRT is displayed by the programmer 110 at the physician's request.

In the embodiments of FIG. 1 and FIG. 2, the determination of battery impedance at RRT (step 240) and determination of "time to RRT" (step 290) are based on the assumption that the measured battery current of step 235 remains constant during the time interval following interrogation and the onset of RRT.

As time passes, due to the normal decline of battery voltage, the battery current drain is affected by charge pump starvation and the reduced current consumption of the ohmic circuitry. The ohmic circuitry comprises the non-pulse digital circuits whose current consumption is independent of the pacing activity. These circuits generally obey ohms law, whereby:

$$I_{CONSUMED} = E_{BAT}/R_{OHMIC-CIRCUITS}$$

That decline affects the shape of the actual battery current drain curve for the device.

In a preferred embodiment, the present invention more accurately predicts the time to the RRT by employing a computer simulation of the operation of the implantable device to more accurately determine the current drain on the battery.

Figure 5:
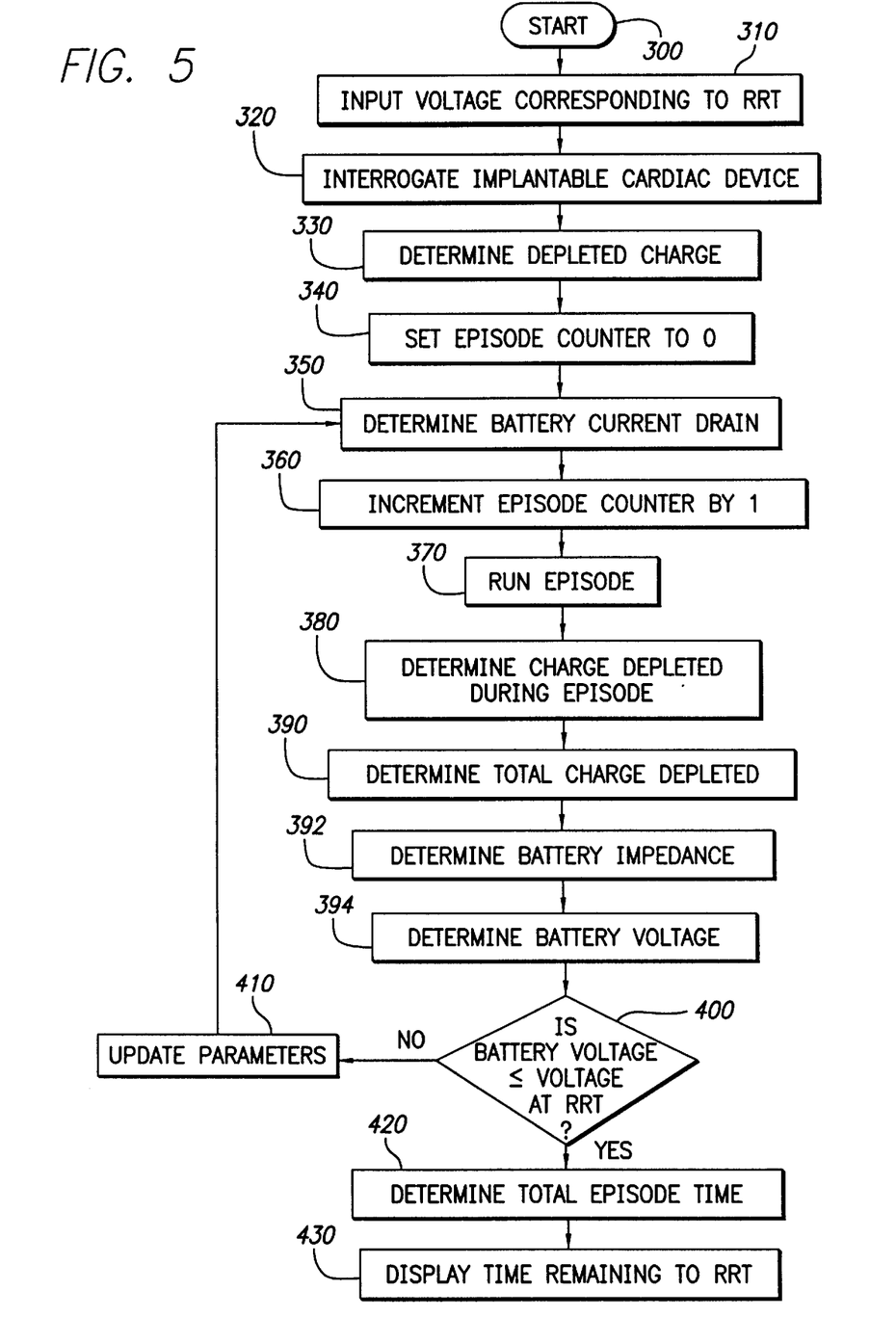
FIG. 5 is a logic flow diagram of a routine executed by the controller of FIG. 1 for determining the time remaining to a battery's recommended replacement time to a second approximation.

It will be seen from the description of FIG. 5, that the computer simulation of the present invention closely approximates the operation of the implantable cardiac device for a simulated pre-set time period or episode and then calculates the charge depleted during that simulated time period. That value is added to the charge depleted up to interrogation.

The computer simulation of the present approach advantageously accounts for the effects of delivered therapy and time on the battery current drain to more accurately predict the time remaining to the RRT. To determine the battery current drain more accurately the programmer accounts for charge pump starvation, the ohmic resistance of the implantable device along with the battery's internal impedance, the therapeutic pulse width, the therapeutic pulse amplitude, the lead impedance(s) and the programmed rate of stimulation delivery. Each subsequent calculation of the current drain includes the simulated effect of each delivered therapy on each parameter. The current drain on the battery is recalculated after each episode.

As stated, after each episode the charge depleted during that episode is calculated and added to the actual battery charge depleted at the time of interrogation. That cumulative depleted charge is used to determine the new battery impedance which in turn is used to calculate the new battery voltage. These newly calculated battery voltages are used to identify when RRT has been reached. At that point, the time frames represented by each simulated episode can be added together, or the number of simulated episodes can be counted and the time frame of one episode can be multiplied by the number of episodes to obtain the forecasted time remaining to the RRT.

In FIG. 5, the preferred embodiment is depicted as a logic flow diagram representing a program executed by the controller 150 which includes a computer simulation of the device 10 executed by the programmer 110.

After a start 300, at a step 310 a user inputs into the controller 150 a voltage corresponding to the battery voltage at the RRT by way of the user interface 190. At a step 320 the programmer 110 of the present embodiment interrogates the implantable cardiac stimulating device 10 to retrieve data stored in the memory 90. That data, in addition to providing the programmer 110 with battery parameters, also includes data concerning the therapeutic pulse width, amplitude, the programmed delivery rate of therapeutic shocks, and lead impedance. At a step 330, the controller 150 determines the charge depleted by following the same procedure as step 270 of FIG. 2.

At a step 340, a counter is set to zero. The counter is used to record how many computer simulated episodes have been executed. At a step 350, the controller 150 calculates battery current drain as a function of the ohmic resistance of the implanted cardiac device 10, battery voltage, the pulse width of therapeutic shocks, the therapeutic pulse amplitude, the preprogrammed rate of therapy delivery, and lead impedance in a known manner. At a step 360, the counter is incremented by 1. At a step 370, a computer simulated episode of cardiac stimulation for a predetermined time frame of, for example, an hour or a day, is initiated by controller 150.

At a step 380, the controller 150 determines the charge depleted for the simulated time frame. At a step 390, the controller 150 sums the battery charge depleted up to the time of interrogation with the simulated battery charge depleted during the simulated time frame to achieve a cumulative depleted charge record. At a step 392, the controller 150 determines the new battery impedance based on the new total charge depleted. At a step 394, the controller 150 determines the new battery voltage based on the new battery impedance. At a test 400, the battery voltage is compared to the previously input battery voltage corresponding to RRT (in step 310). If the battery voltage is still greater than the voltage corresponding to RRT, the simulation parameters are updated to account for decline in battery voltage during the simulated time frame. Both the charge pump current and the quiescent current are affected by the battery voltage decline. The routine cycles through the steps 350 to 400 until the determined battery voltage has declined to the voltage corresponding to RRT (input at step 310).

At that time, at a step 420, the total simulated episode time is calculated by multiplying the total number of episodes as tracked by the counter and the simulated time frame of each episode. The result of that operation represents the time remaining to the RRT. As an alternate to multiplying the time frame represented by each episode by the number of episodes, the system could (instead of counting the number of episodes) keep a running total of the time frame represented by the simulations. At a step 430, the time remaining to the RRT is displayed to the user. It is readily apparent that the smaller the time frame chosen to represent each episode, the more accurate the time remaining to the RRT prediction will be because any overlap with the battery voltage at the RRT will be minimized and the simulated current drain curve will be truer.

It is desirable that the simulated time frame of each episode be as short as practically possible in order to maximize the accuracy of the time remaining time to the RRT prediction. Because the present embodiment employs a computer simulation of stimulation episodes, a more powerful controller is needed to enable calculation of the time remaining to the RRT within a practical time period.

Figure 6:
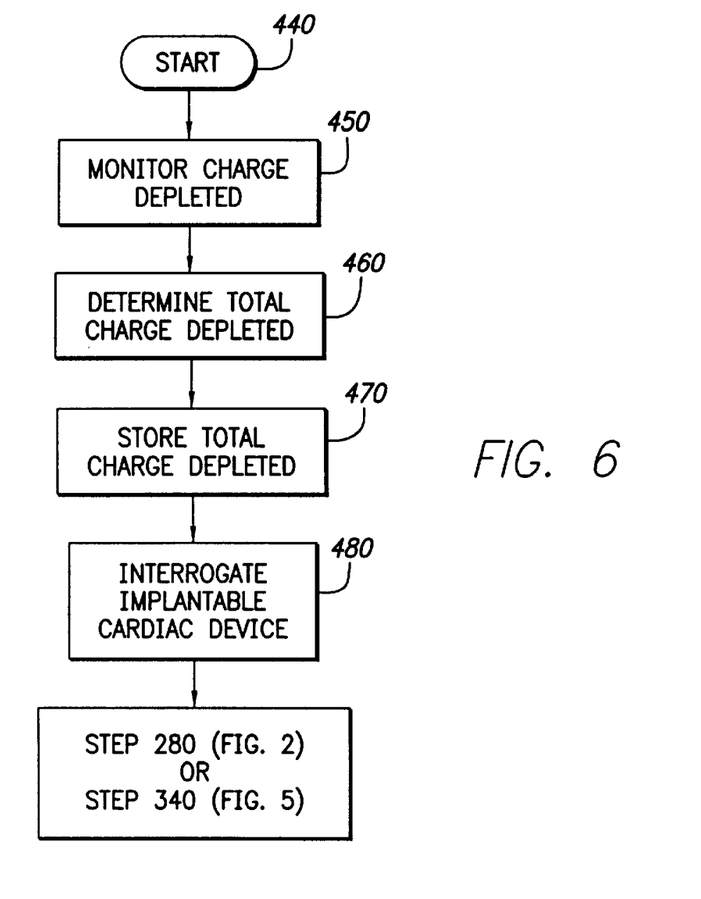
FIG. 6 is a logic flow diagram of a routine executed by the present invention for determining the time remaining to a battery's recommended replacement time to a third approximation.

In another embodiment, the present invention provides a more accurate determination of the time remaining to the RRT by adding to either the first or second embodiment an implantable cardiac stimulating device that is able to record and store data on how much battery charge has been expended. In FIG. 6, a logic flow diagram representing a system for determining the time remaining to the RRT is described.

After a start 440, at a step 450 the implantable cardiac device 10 monitors the battery charge depleted with each therapeutic pulse delivered and the charge necessary for monitoring operations and logic operations. At a step 460, each new determination of charge depleted is summed with previous determinations. At a step 470, the resulting sum is stored in a memory 90. At a step 480, the programmer 110 interrogates the implantable cardiac device 10 to retrieve the data stored in memory 90. The programmer of the present invention may then use that data to determine the time remaining to the RRT according to the embodiment, shown in FIG. 2, beginning at the step 280 or the embodiment, shown in FIG. 5, beginning at the step 340.

In yet another embodiment, the present invention advantageously uses historical event data to more accurately represent battery charge depletion for realistic heart-pacemaker scenarios and for implantable cardiac devices that can tailor therapy according to an individual's lifestyle. All three previously discussed embodiments (i.e., the Direct Calculation of the prior art method, the Computer Simulation method of the preferred embodiment, and the Charge Counting method) are enhanced by allowing for pacemaker inhibition and allowing for elevated and lowered pacing rates. The previous embodiments are further enhanced by allowing for spontaneous physiologic changes in capture thresholds.

Figure 7:
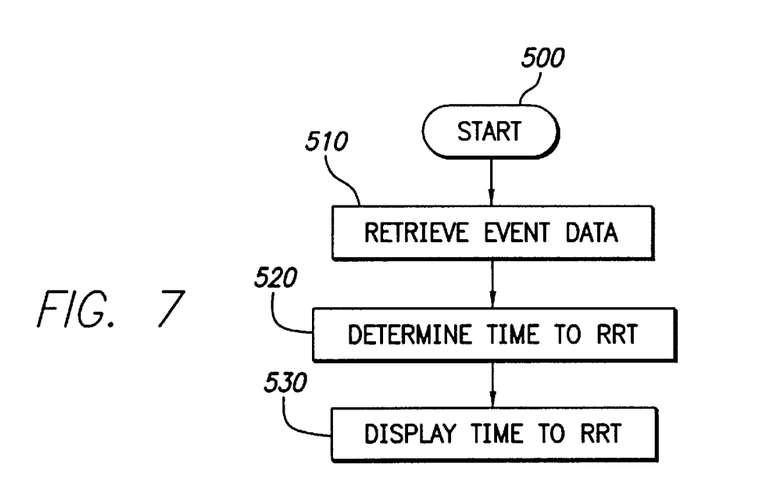
FIG. 7 is a logic flow diagram of a routine executed by the controller of FIG. 1 for determining the time remaining to a battery's recommended replacement time to a fourth approximation.

In FIG. 7, a logic flow diagram representing a system for determining the time remaining to RRT is described based on historical data stored in the pacemaker.

After a start 500, at a step 510 telemetered event data is extracted from the implantable cardiac stimulating device 10. The event data includes average pacing rate data and/or percent pacing data. At a step 520, the time remaining to the RRT is determined by incorporating the average pacing rate and/or percent pacing data and/or average pacing pulse amplitude into the RRT determinations described above according to the following relationship:

$$I_{predicted} = \% \ Pacing * I_{measured} * (RATE_{avg}/RATE_{programmed})$$

The average pacing rate reflects more accurately true pacemaker performance because the pacemaker sometimes paces at rates higher or lower than the programmed rate. An elevated pacing rate can be due to the P-wave tracking effect where a healthy sinus node accelerates in response to physiologic demands and ventricular pacing tracks the atrial rate. Elevated rates can also be due to rate modulated pacing where the pacemaker automatically increases its rate in response to measured or inferred physiologic demands (e.g., 02 saturation, activity).

A lowered pacing rate can be due to the operation of a sleep mode function in the pacemaker. This feature automatically adjusts the pacing rate to the patient's circadian cycle.

Alternatively, the time remaining is determined by incorporating the average pacing amplitude according to the following relationship.

$$I_{predicted} = I_{measured} * (E_{pulse\_avg}/E_{pulse\_programmed})$$

The average pacing amplitude more accurately reflects true pacemaker performance because the pacemaker sometimes paces at pulse voltage amplitudes different than the programmed amplitude. The varying rates can be due pacemaker adaptation to spontaneous physiologic changes in the capture threshold.

Since the amount of charge delivered to the patient's heart can be varied by keeping the amplitude fixed and thereafter adjusting the pulse width, another embodiment includes determining the time remaining by incorporating the average pacing pulse width according to the following relationship.

$$I_{predicted} = I_{measured} * (PW_{pulse\_avg}/PW_{pulse\_programmed})$$

Likewise one of skill in the art could apply the above techniques to keep track of the amount of charge (and, in turn, current drain) that is used with each shocking pulse of a ICD device. This charge (or current drain) information, coupled with a history of frequency of shocks and waveshape, can be used to more accurately predict the amount of charge (or current drain) needed until RRT is reached.

Percent pacing data extracted from event data is also incorporated to account for pacemaker inhibition by native heart activity. At a step 530, the time remaining to RRT is displayed to the physician.

Thus, a system and method for determining and displaying the time remaining to the recommended replacement time of a battery of a implantable cardiac stimulating device are provided. One skilled in the art will appreciate that the present invention can be practiced by other than the described embodiments, which are presented for purposes of illustration and not of limitation, and the present invention is limited only by the Claims that follow.

What is claimed is:

1. A system for providing a time remaining to a recommended battery replacement time of an implantable stimulation device, the system comprising:

pulse generating means for generating stimulation pulses to a patient's body tissue in accordance with the patient's needs;e a battery for powering the pulse generating means;

monitoring means, coupled to the pulse generating means and the battery, for monitoring a plurality of operating and battery parameters;

simulation means for simulation the operation of the pulse generating means based upon at least one operating characteristic of the device and at least one parameter representative of the state of the battery;

predicting means for forecasting a time remaining to the recommended replacement time of the battery based upon the simulation of the operation of the pulse generating means; and display means for displaying the time remaining to the recommended replacement time of the battery.

2. The system of claim 1, wherein the monitoring means comprises:

means for monitoring at least battery voltage, current drain on the battery, and internal battery impedance; and wherein the predicting means includes means for forecasting the time remaining to the recommended replacement time based on previous current drain usage.

3. The system of claim 1, wherein the monitoring means comprises:

means for monitoring a rate of stimulation pulses; and wherein the predicting means includes means for forecasting the time remaining to the recommended replacement time based on a previous rate of the stimulation pulses.

4. The system of claim 1, wherein the monitoring means comprises:

means for monitoring at least one amplitude or pulse width of the stimulation pulses; and wherein the predicting means includes means for forecasting the time remaining to the recommended replacement time based on the at least one of a previous amplitude or pulse width of the stimulation pulses.

5. The system of claim 4, further comprising:

means for varying at least one of the amplitude or the pulse width of the stimulation pulses in accordance with the patient's threshold; and wherein the predicting means includes means for forecasting the time remaining to the recommended replacement time based on at least one of the varying amplitude or pulse width of the stimulation pulses.

6. The system of claim 4, further comprising:

means for varying one of the amplitude or the pulse width of the stimulation pulses in accordance with the patient's threshold; and wherein the monitoring means comprises means for monitoring one of the average amplitude or average pulse width of the stimulation pulses; and wherein the predicting means includes means for forecasting the time remaining to the recommended replacement time based on the one of the varying amplitude or pulse width of the stimulation pulses.

7. The system of claim 1, further comprising:

means for varying the rate of stimulation pulses based on physiological need;

wherein the monitoring means comprises means for monitoring the average rate of the stimulation pulses; and wherein the predicting means includes means for forecasting the time remaining to the recommended replacement time based on the average rate of the stimulation pulses.

8. The system of claim 1, wherein the monitoring means comprises:

means for monitoring a percentage of paced events; and wherein the predicting means includes means for forecasting the time remaining to the recommended replacement time based on the percentage of paced events.

9. The system of claim 1, further comprising:

means for lowering the rate during sleep;

wherein the monitoring means comprises means for monitoring an average rate of stimulation pulses over at least approximately one day; and wherein the predicting means includes means for forecasting the time remaining to the recommended replacement time based on the average rate of stimulation pulses over at least the previous one day.

10. The system of claim 1, wherein:

the pulse generating means includes means for generating stimulation pulses in both a patient's atrium and ventricle in the absence of P-waves and R-waves, respectively, and further includes means for inhibiting the generation of an atrial and ventricular stimulation pulses in the presence of P-waves and R-waves, respectively;

the monitoring means comprises means for monitoring a percentage of atrial and ventricular paced events; and the predicting means includes means for forecasting the time remaining to the recommended replacement time based on the percentage of atrial and ventricular paced events.

11. The system of claim 1, wherein the pulse generating means includes means for generating high amplitude shocking pulses, wherein the monitoring means comprises:

means for monitoring one of frequency of therapy shocks delivered, therapeutic shock amplitude, and therapeutic shock waveform; and wherein the predicting means includes means for forecasting the time remaining to the recommended replacement time based on the selected one of frequency of therapy shocks delivered, therapeutic shock amplitude, and therapeutic shock waveform.

12. The system of claim 1, wherein the implantable stimulation device includes ohmic circuits and charge pump circuitry which have current drain characteristics which vary as a function of declining battery voltage, wherein the monitoring means comprises:

means for revising the simulated device operating parameters after each simulated time frame to include changes to such parameters as a result of the declining simulated battery voltage and charge depleted during each time frame; and wherein the simulation means simulates the operation of the pulse generator means for a plurality of time frames based on the device operating parameter; and wherein the predicting means includes means for forecasting the time remaining to the recommended replacement time based on the simulated operation and the declining battery voltage.

13. A method for determining a time remaining to a recommended replacement time of a battery of an implantable cardiac stimulating device, comprising the steps of:

monitoring device operating and battery parameters from the stimulating device;

determining a first amount of battery charge actually depleted as a function of the battery parameters, the battery parameters including battery voltage, battery current drain, and internal battery impedance;

determining a second amount of battery charge corresponding to a point in time at which the stimulating device is recommended for replacement;

determining an amount of battery charge remaining to the recommended battery replacement time by subtracting the second amount of battery charge from the first amount of battery charge; and predicting the time remaining to the recommended battery replacement time based on the amount of battery charge remaining and the monitored device operating parameters.

14. The method of claim 13, wherein the step of predicting the time remaining to the recommended battery replacement time further comprises the steps of:

simulating the operation of the stimulating device for a plurality of time frames based on the device operating parameters; and revising the device operating parameters after each simulated time frame to include changes to such parameters as a result of the additional battery charge depleted during each time frame.

15. The method of claim 14, wherein the step of simulating the operation of the stimulation device comprises the steps of:

determining for each time frame the battery current drain as a function of the device operating parameters;

determining the battery charge depleted in each time frame based on the battery current drain determined for that time frame;

adding the battery charge depleted in each time frame to the first battery charge to get a predicted total charge needed for each additional time frame;

determining a battery impedance and from that determining a battery voltage;

comparing battery voltage with a target battery voltage associated with RRT;

repeating the foregoing steps until the calculated battery voltage is less than or equal to the target voltage;

determining the total simulated time of all time frames; and displaying the total simulated time frame as the time remaining to the recommended battery replacement time.

16. The method of claim 13, wherein the device operating parameters include parameters selected from the group consisting of programmed rate of therapy delivery, programmed therapeutic shock amplitude, therapeutic shock waveform, and the ohmic resistance of the implantable cardiac stimulating device.

17. The method of claim 13, wherein determining the first battery charge depleted comprises retrieving from the implantable cardiac device a cumulative record of battery charge depleted.

18. A system for predicting a time remaining to a recommended replacement time of a battery of an implantable medical device, the system comprising:

means for inputting a request that a prediction be made of the time remaining to the recommended replacement time of the battery;

means, responsive to receipt of the request, for predicting the time remaining to the recommended replacement time of the battery, wherein the means for predicting comprises:

means for determining at least one operating characteristic of the device and at least one parameter representative of the state of the battery;

means for estimating a time remaining to the recommended replacement time of the battery based on the at least one operating characteristic of the device and the at least one parameter representative of the state of the battery, wherein the implantable medical device includes a pulse stimulation unit for providing stimulation pulses, and wherein the at least one operating characteristic of the pulse generating unit comprises a percentage of paced events, wherein the percentage of paced events includes one or more of a percentage of atrial paced events and a percentage of ventricular paced events; and means for outputting a signal representative of the predicted time remaining to the recommended replacement time of the battery.

19. The system of claim 18, wherein the system is part of an external programmer device.

20. The system of claim 19, wherein the means for predicting the time remaining to the recommended replacement time of the battery includes means for interrogating the implantable medical device to determine at least one parameter representative of the state of the battery for use in making the prediction.

21. The system of claim 18, wherein the implantable medical device is capable of varying the rate, amplitude or pulse width of the stimulation pulses and wherein the at least one operating characteristic of the pulse generating unit is selected from a group consisting of: a time-varying rate of the stimulation pulses, a time-varying amplitude of the stimulation pulses, and a time-varying pulse width of the stimulation pulses.

22. The system of claim 18, wherein the implantable medical device is capable of varying the rate, amplitude or pulse width of the stimulation pulses and wherein the at least one operating characteristic of the pulse generating unit is selected from a group consisting of: an average rate of the stimulation pulses, an average amplitude of the stimulation pulses, and an average pulse width of the stimulation pulses.

23. The system of claim 22, wherein the averages and determined over at least one day.

24. The system of claim 23, wherein the averages are determined over approximately one previous day.

25. The system of claim 18, wherein the implantable medical device is capable of generating high amplitude shocking pulses and wherein the at least one operating characteristic of the pulse generating unit is selected from a group consisting of: a frequency of therapy shocks delivered, a therapeutic shock amplitude, and a therapeutic shock waveform.

26. The system of claim 18, wherein means for predicting a time remaining to the recommended replacement time of the battery includes means for simulating the operation of the implantable medical device based upon the at least one operating characteristic of the device and the at least one parameter representative of the state of the battery.

27. The system of claim 26, wherein the at least one parameter representative of the state of the battery permits a determination of the amount of charge in the battery and wherein means for simulating the operation of the implantable medical device includes:

means for determining a current amount of charge in the battery based upon the at least one parameter representative of the state of the battery;

means for defining a plurality of time frames;

means for determining for each time frame an amount of charge expected to be depleted from the battery based on the at least one operating characteristic of the device; and means for determining how many time frames elapse before the battery falls below a predetermined minimum acceptable amount of charge.

28. The system of claim 27, wherein the stimulation device includes ohmic circuits and charge pump circuitry which have current drain characteristics which vary as a function of declining battery voltage and wherein the means for determining for each time frame an amount of charge expected to be depleted from the battery operates by revising simulated device operating parameters after each time frame to include changes to the simulated device operating parameters as a result of a declining simulated battery voltage and any charge depleted during each time frame.

29. The system of claim 18, wherein the at least one parameter representative of the state of the battery is selected from a group consisting of: battery voltage, current drain on the battery, and internal battery impedance.

30. A method for predicting a time remaining to a recommended replacement time of a battery of an implantable medical device, the method comprising the steps of:

inputting a request that a prediction be made of the time remaining to the recommended replacement time of the battery;

predicting, in response to receipt of the request, the time remaining to the recommended replacement time of the battery, wherein the step of predicting comprises:

determining at least one operating characteristic of the device and at least one parameter representative of the state of the battery; and simulating the operation of the implantable medical device based upon the at least one operating characteristic of the device and the at least one parameter representative of the state of the battery;

estimating a time remaining to the recommended replacement time of the battery based on the at least one operating characteristic of the device and the at least one parameter representative of the state of the battery; and outputting a signal representative of the predicted time remaining to the recommended replacement time of the battery.

31. The method of claim 30 performed by an external programmer device.

32. The method of claim 31, wherein the step of predicting the time remaining to the recommended replacement time of the battery includes the step of interrogating the implantable medical device to determine at least one parameter representative of the state of the battery for use in making the prediction.

33. The method of claim 30, wherein the at least one parameter representative of the state of the battery permits a determination of the amount of charge in the battery and wherein the step of simulating the operation of the implantable medical device includes the steps of:

determining a current amount of charge in the battery based upon the at least one parameter representative of the state of the battery;

defining a plurality of time frames;

determining for each time frame an amount of charge expected to be depleted from the battery based on the upon the at least one operating characteristic of the device; and determining how many time frames elapse before the battery falls below a predetermined minimum acceptable amount of charge.

34. The method of claim 33, wherein the implantable medical device includes ohmic circuits and charge pump circuitry which have current drain characteristics which vary as a function of declining battery voltage and wherein the step of determining for each time frame an amount of charge expected to be depleted from the battery operates by revising simulated device operating parameters after each time frame to include changes to the simulated device operating parameters as a result of a declining simulated battery voltage and any charge depleted during each time frame.

35. A system for predicting a time remaining to a recommended replacement time of a battery of an implantable medical device, the system comprising:

an input unit for inputting a request that a prediction be made of the time remaining to the recommended replacement time of the battery;

a prediction unit, operative in response to receipt of the request, for predicting the time remaining to the recommended replacement time of the battery, wherein the a prediction unit comprises:

a determination unit for determining at least one operating characteristics of the device and at least one parameter representative of the state of the battery; and a simulation unit for simulating the operation of the implantable medical device based upon the at least one operating characteristic of the device and the at least one parameter representative of the state of the battery;

an estimation unit for estimating a time remaining to the recommended replacement time of the battery based upon the simulation of the operation of the implantable medical device; and an output unit for outputting a signal representative of the predicted time remaining to the recommended replacement time of the battery.

36. The system of claim 35, wherein the system is part of an external programmer device.

37. The system of claim 36, wherein the prediction unit includes an interrogation unit for interrogating the implantable medical device to determine at least one parameter representative of the state of the battery for use in making the prediction.

38. The system of claim 35, wherein the at least one parameter representative of the state of the battery permits a determination of the amount of charge in the battery and wherein the simulation unit includes:

a charge determination unit for determining a current amount of charge in the battery based upon the at least one parameter representative of the state of the battery;

a time frame unit for defining a plurality of time frames;

a depletion determination unit for determining for each time frame an amount of charge expected to be depleted from the battery based on the upon the at least one operating characteristic of the device; and a threshold determination unit for determining how many time frames elapse before the battery falls below a predetermined minimum acceptable amount of charge.

39. The system of claim 38, wherein the implantable medical device includes ohmic circuits and charge pump circuitry which have current drain characteristics which vary as a function of declining battery voltage and wherein the depletion determination unit operates by revising simulated device operating parameters after each time frame to include changes to the simulated device operating parameters as a result of a declining simulated battery voltage and any charge depleted during each time frame.

* * * * *